US006800776B1

(12) United States Patent
Jong et al.

(10) Patent No.: US 6,800,776 B1
(45) Date of Patent: Oct. 5, 2004

(54) METHOD FOR THE PREPARATION OF FERROCENYL SUBSTITUTED STYRENE

(75) Inventors: Shean-Jeng Jong, Tao-Yuan (TW); Tseng-Rong Wu, Tao-Yuan (TW)

(73) Assignee: Chung-Shan Institute of Science & Technology, Tao-Yuan (TW)

( * ) Notice: Subject to any disclaimer, the term of this patent is extended or adjusted under 35 U.S.C. 154(b) by 0 days.

(21) Appl. No.: 10/667,590

(22) Filed: Sep. 23, 2003

(51) Int. Cl.[7] .......................... C07F 17/02; B01J 31/00
(52) U.S. Cl. .................. 556/143; 556/140; 502/224
(58) Field of Search ................... 556/140, 143; 502/224

(56) References Cited

U.S. PATENT DOCUMENTS

| | | | | |
|---|---|---|---|---|
| 2,567,890 A | * | 9/1951 | Myklestad | 123/378 |
| 4,219,490 A | * | 8/1980 | Gotzmer, Jr. | 556/144 |
| 6,211,392 B1 | * | 4/2001 | Fang et al. | 556/143 |

FOREIGN PATENT DOCUMENTS

WO    WO 96/11935    *   4/1996

OTHER PUBLICATIONS

Jong et al., Journal of Organic Chemistry, vol. 66, No. 10, pp. 3533–3537 (2001).*

* cited by examiner

*Primary Examiner*—Porfirio Nazario-Gonzalez
(74) *Attorney, Agent, or Firm*—Bacon & Thomas PLLC

(57) ABSTRACT

Ferrocenecarbonyl and toluene bromide are reacted in an ether solvent and in the presence of magnesium metal as a catalyst. The liquid portion of the reaction mixture is introduced into a silica gel column, wherein the weak acidity of the silica gel is able to dehydrate the reaction intermediate ferrocenyl alcohol product. The column is eluted with ethyl acetate/n-hexane, and after evaporating the solvent from the eluate collected, a purified ferrocenyl substituted styrene is obtained.

12 Claims, No Drawings

US 6,800,776 B1

METHOD FOR THE PREPARATION OF FERROCENYL SUBSTITUTED STYRENE

FIELD OF THE INVENTION

The present invention relates to a method for manufacturing ferrocenyl substituted styrene. More particularly, the present invention relates to a method for manufacturing ferrocenyl substituted styrene without heating or vacuum sublimation.

BACKGROUND OF THE INVENTION

A ferrocenyl double bond compound having the following structure can be utilized in various applications:

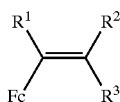

wherein Fc is ferrocenyl, for examples the applications disclosed in FR 2,567,890 (1986), U.S. Pat. No. 4,219,490 (1980) and Czech. 175,857 (1979). C. A. 90,138026c discloses that a ferrocenyl ethylene compound can be used to synthesize ferrocenyl derivatives.

JP 7-309915 (1995) discloses a high refractive index resin of a polyvinylferrocene copolymer.

JP 8-029372 (1996) discloses an enzyme electrode made from a copolymer of a vinyl monomer having a ferrocene and dodecyl methacrylate.

An article, Nature 330,360 (1987), discloses that the following compound has non-linear optical properties:

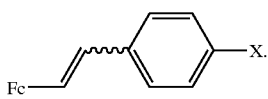

Another article, Inorg Chim. Acta, 242(1–2), 43 (1996), discloses a non-linear optical compound having the following structure:

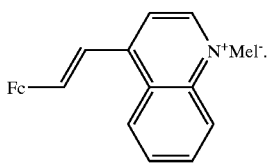

A further article, J. Chem. Soc., Chem. Commun., 1122 (1987), discloses redox-active crown ethers having the following structure:

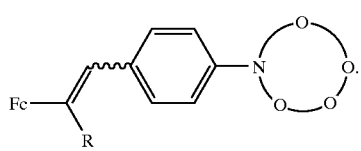

WO 96/11935 (1996) discloses compounds having the following structure, the methods of preparation and pharmaceutical compositions containing same:

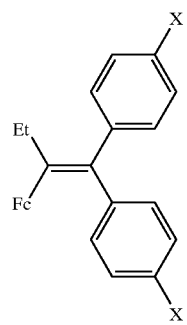

The derivatives of this patent application are suitable for the preparation of antitumoral drugs for use, in particular, in the treatment of estrogen-dependent breast cancers.

An article, J. Org. Chem., 66, 3533 (2001), discloses a method for synthesizing ferrocenyl styrene by reacting ferrocenecarbonyl and toluene bromide, the reaction of which can be represented as follows:

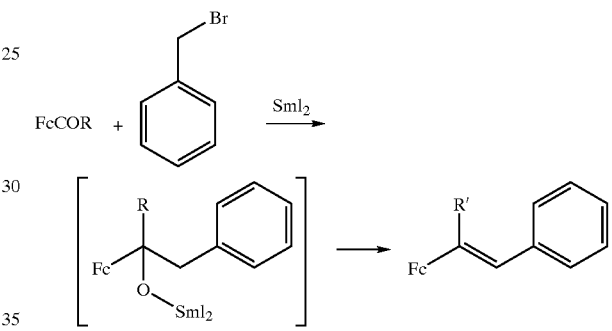

In this method the reaction is carried out in tetrahydrofuran (THF) and in the presence of samarium diiodide as a catalyst, and then the reaction mixture is dehydrated under reflux in air to obtain ferrocenyl styrene. The catalyst used, samarium diiodide, is expensive and will undergo hydrolysis in air or moisture U.S. Pat. No. 6,211,392B1 discloses a method of manufacturing ferrocenyl-1,3-butadiene, in which a ferrocenecarbonyl is reacted with an allyl halide in a polar aprotic solvent lacking a carbonyl group in the presence of samarium diiodide as a catalyst. The method of this US patent has a relatively high yield; however, the catalyst used, samarium diiodide, is expensive and will undergo hydrolysis in air or moisture.

There is still a need in the industry for developing an easier method for the preparation of ferrocenyl styrene.

SUMMARY OF THE INVENTION

The present invention provides a method for synthesizing ferrocenyl substituted styrene having the following Formula III, which comprises: a) reacting ferrocenecarbonyl having the following Formula I with toluene halide having the following Formula II in an ether solvent and in the presence of magnesium as a catalyst; b) introducing a liquid portion of the resulting reaction mixture into a silica gel column; c) eluting the silica gel column with a solvent of low polarity; d) collecting the resulting. eluate from the column; e) and evaporating the solvent from the eluate to obtain a solid comprising ferrocenyl substituted styrene (III):

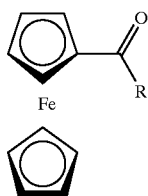

(I)

wherein R is hydrogen or C1–C4 alkyl;

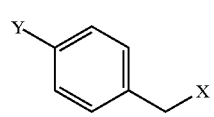

(II)

wherein X is a halogen; Y is a halogen, hydrogen or C1–C4 alkyl;

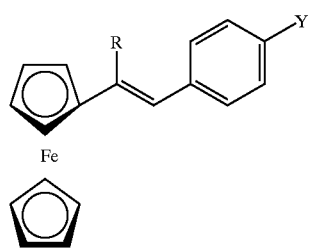

(III)

wherein R and Y are defined as above.

Preferably, X is bromine, and Y is hydrogen or C1–C4 alkyl.

Preferably, R is hydrogen or methyl.

Preferably, the ether solvent is tetrahydrofuran or ethyl ether, and more preferably, tetrahydrofuran.

Preferably, said solvent of low polarity is n-hexane, ethyl acetate or a mixture of them.

Preferably, said reaction in step a) is carried out at room temperature for a period of 3–48 hours.

Preferably, said liquid portion is kept in the silica gel column for a period of 6–96 hours in step b).

Preferably, a mole ratio of said toluene halide (II) to said ferrocenecarbonyl (I) in said reaction in step a) ranges from 0.1 to 20, and more preferably, is about 1.5.

Preferably, a mole ratio of said magnesium catalyst to said ferrocenecarbonyl (I) in said reaction in step a) ranges from 0.1 to 20, and more preferably, is about 3.

In the method of the present invention, the reaction mixture in step a) does not need to be heated under refluxing, and the catalyst used in a common alkaline earth metal.

DETAILED DESCRIPTION OF THE INVENTION

A synthesis method for ferrocenyl substituted styrene according to one of the preferred embodiments of the present invention can be represented by the following reaction formula:

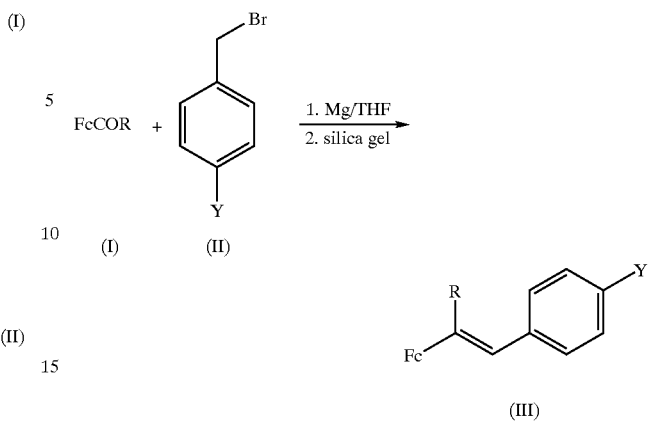

wherein Fc is ferrocenyl, Y and R are defined as above.

Ferrocenecarbonyl (I) reacts with toluene bromide (II) having a substituent, Y, in the presence of magnesium metal as a catalyst and in an ether solvent such as tetrahydrofuran (THF). The liquid portion of the reaction mixture is introduced into a silica gel column, and is kept in the silica gel column for a certain period of time such that the silica gel having a weak acidity dehydrates the reaction intermediate, ferrocenyl alcohol, into ferrocenyl substituted styrene (III) having a lower polarity. Next, an eluent having a low polarity such as n-hexane, ethyl acetate or a mixture thereof is used to desorb the product (III), and the eluate is collected. After removing the solvent by evaporation, a purified ferrocenyl substituted styrene product is obtained. The silica gel used in the present invention is not limited and can be an arbitrary commercial silica gel. The invented method is simple to be operated and requires no refluxing or vacuuming. Moreover, the catalyst used is stable and is not expensive.

In the method of the present invention, a suitable amount of the ether solvent for in the reaction is 1–20 liters, and preferably is about 15 liters, per mole of the ferrocenecarbonyl (I).

The present invention can be further elaborated by way of the following examples which are for illustrative purposes only and not for limiting the scope of the present invention.

EXAMPLE 1

Synthesis of 1-ferrocenyl-1-methyl,2-styrene 72 mg (3.0 mmole) of magnesium metal was placed in a 50 ml round bottom flask. 228 mg (1.0 mmole) of ferrocenyl methyl ketone and 256.5 mg (1.5 mmole) of toluene bromide were dissolved in 15 ml of THF. The resulting mixture was poured into the round bottom flask containing the magnesium metal while stirring at room temperature for 12 hours. After 12-hour stirring, the cover of the flask was opened, and the liquid portion of the reaction mixture was introduced into a silica gel column, which had been wetted with n-hexane. All the liquid migrated into the silica gel, and the column was placed still for 48 hours. Next, the column was eluated with a mixed solvent of ethyl acetate and n-hexane (1:4 by volume). After evaporating the solvent from the eluate collected from the elution, 275 mg (0.91 mmole) of a purified title product was obtained with a yield of 91%.

Melting poitn: 64~66° C.

$^1$H-NMR(CDCl$_3$) δ:

2.13(3H, s)

4.05(5H, s)
4.18(2H, s)
4.39(2H, s)
6.64(1H, s)
7.26~7.10(5H, m)
IR(KBr):1627 cm$^{-1}$
FAB-MS m/z 302(M$^+$)

EXAMPLE 2

Synthesis of 1-ferrocenyl, 2-styrene 72 mg (3.0 mmole) of magnesium metal was placed in a 50 ml round bottom flask. 214 mg (1.0 mmole) of ferrocenaldehyde and 256.5 mg (1.5 mmole) of toluene bromide were dissolved in 15 ml of THF. The resulting mixture was poured into the round bottom flask containing the magnesium metal while stirring at room temperature for 12 hours. After 12-hour stirring, the cover of the flask was opened, and the liquid portion of the reaction mixture was introduced into a silica gel column, which had been wetted with n-hexane. All the liquid migrated into the silica gel, and the column was placed still for 48 hours. Next, the column was eluated with a mixed solvent of ethyl acetate and n-hexane (1:4 by volume). After evaporating the solvent from the eluate collected from the elution, 232 mg (0.80 mmole) of a purified title product was obtained with a yield of 80%.

Melting point: 118° C.
$^1$H-NMR(CDCl$_3$) δ:
4.16(5H, s)
4.30(2H, t)
4.49(2H, t)
6.72(1H, d)
6.90(1H, d)
7.47~7.22(5H, m)
IR(KBR):1636, 1597 cm$^{-1}$
FAB-MS m/z 288(M$^+$)

What is claimed is:

1. A method for synthesizing ferrocenyl substituted styrene having the following Formula III, which comprises: a) reacting ferrocenecarbonyl having the following Formula I with toluene halide having the following Formula II in an ether solvent and in the presence of magnesium as a catalyst; b) introducing a liquid portion of the resulting reaction mixture into a silica gel column; c) eluting the silica gel column with a solvent of low polarity; d) collecting the resulting eluate from the column; e) and evaporating the solvent from the eluate to obtain a solid comprising ferrocenyl substituted styrene (III):

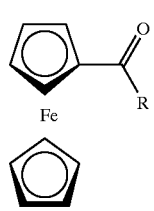

wherein R is hydrogen or C1–C4 alkyl;

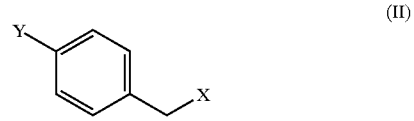

wherein X is a halogen; Y is a halogen, hydrogen or C1–C4 alkyl;

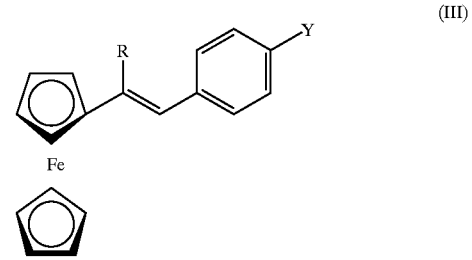

wherein R and Y are defined as above.

2. The method according to claim 1, wherein X is bromine, and Y is hydrogen or C1–C4 alkyl.

3. The method according to claim 1, wherein R is hydrogen or methyl.

4. The method according to claim 1, wherein the ether solvent is tetrahydrofuran or ethyl ether.

5. The method according to claim 4, wherein the ether solvent is tetrahydrofuran.

6. The method according to claim 1, wherein said solvent of low polarity is n-hexane, ethyl acetate or a mixture of them.

7. The method according to claim 1, wherein said reaction in step a) is carried out at room temperature for a period of 3–48 hours.

8. The method according to claim 1, wherein said liquid portion is kept in the silica gel column for a period of 6–96 hours in step b).

9. The method according to claim 1, wherein a mole ratio of said toluene halide (II) to said ferrocenecarbonyl (I) in said reaction in step a) ranges from 0.1 to 20.

10. The method according to claim 9, wherein said mole ratio of said toluene halide (II) to said ferrocenecarbonyl (I) is about 1.5.

11. The method according to claim 1, wherein a mole ratio of said magnesium catalyst to said ferrocenecarbonyl (I) in said reaction in step a) ranges from 0.1 to 20.

12. The method according to claim 11, wherein said mole ratio of said magnesium catalyst to said ferrocenecarbonyl (I) is about 3.

* * * * *